(12) United States Patent
Kim

(10) Patent No.: US 9,724,474 B2
(45) Date of Patent: Aug. 8, 2017

(54) FILTER SYRINGE

(71) Applicant: Zamat Co., Ltd., Seoul (KR)

(72) Inventor: Keun-Bae Kim, Seoul (KR)

(73) Assignee: Zamat Co., Ltd., Seoul (KR)

( * ) Notice: Subject to any disclaimer, the term of this patent is extended or adjusted under 35 U.S.C. 154(b) by 0 days.

(21) Appl. No.: 14/728,170

(22) Filed: Jun. 2, 2015

(65) Prior Publication Data

US 2015/0258280 A1    Sep. 17, 2015

Related U.S. Application Data

(63) Continuation of application No. PCT/KR2013/010669, filed on Nov. 22, 2013.

(30) Foreign Application Priority Data

Dec. 3, 2012  (KR) .......................... 10-2012-0139188
May 24, 2013  (KR) .......................... 10-2013-0058698

(51) Int. Cl.
*A61M 5/31* (2006.01)
*A61M 5/165* (2006.01)
*A61M 5/34* (2006.01)
*A61M 5/32* (2006.01)
*A61M 5/38* (2006.01)

(52) U.S. Cl.
CPC .......... *A61M 5/3145* (2013.01); *A61M 5/165* (2013.01); *A61M 5/3293* (2013.01); *A61M 5/34* (2013.01); *A61M 5/38* (2013.01)

(58) Field of Classification Search
CPC .... A61M 5/3145; A61M 5/3293; A61M 5/38; A61M 5/165; A61M 5/34; A61M 5/329
See application file for complete search history.

(56) References Cited

U.S. PATENT DOCUMENTS 4,332,249 A * 6/1982 Joslin .................. A61M 5/3145
                                                              604/36
9,265,883 B2 * 2/2016 Kim ...................... A61M 5/165

FOREIGN PATENT DOCUMENTS

| JP | 2003-339876 A | 12/2003 |
| KR | 10-2005-0108169 A | 11/2005 |
| KR | 10-2012-0077486 A | 7/2012 |
| WO | 2012/138177 A2 | 10/2012 |

* cited by examiner

*Primary Examiner* — Laura Bouchelle
*Assistant Examiner* — Anh Bui
(74) *Attorney, Agent, or Firm* — Jefferson IP Law, LLP

(57) ABSTRACT

A syringe with a filter is disclosed. When liquid medicine for treatment such as an analgesic is suctioned into the syringe by using a syringe needle and then injected into a human body through the syringe needle, foreign substances generated in an ampule and the like are filtered in the syringe prior to the liquid medicine being injected into the human body as the foreign substances are suctioned into the syringe through the syringe needle. In addition, the filter is configured so that the filter can be installed into the syringe with ease.

8 Claims, 6 Drawing Sheets

FILTER SYRINGE

CROSS-REFERENCE TO RELATED APPLICATION(S)

This application claims the benefit under §365(c) of an international application filed on Nov. 22, 2013 and assigned serial number PCT/KR2013/010669, which claims the benefit of a Korean patent application filed on Dec. 3, 2012 in the Korean Intellectual Property Office and assigned serial number 10-2012-0139188 and of a Korean patent application filed on May 24, 2013 in the Korean Intellectual Property Office and assigned serial number 10-2013-0058698, the entire disclosures of which are hereby incorporated by reference.

TECHNICAL FIELD

The present disclosure relates to a syringe, and more particularly, to a syringe, in which, when liquid medicine for treatment such as an analgesic is suctioned into a syringe by using a syringe needle and then injected into a human body through the syringe needle, foreign substances generated in an ampule and the like are filtered in the syringe when the liquid medicine is injected into the human body and when the foreign substances are suctioned into the syringe through the syringe needle.

In addition, a filter for the filtering is installed in the syringe such that the syringe can be used for injecting medicine into a human body as well as via a catheter, and the filter is prevented from being detached from the syringe during suctioning and injecting through a simple insertion of the filter in the syringe.

BACKGROUND

In general, a syringe includes a syringe body and a syringe needle, and is used in a hygienically packaged or stored state after coupling the syringe needle to the syringe or in a state that the syringe needle is assembled with the syringe when directly injecting the liquid medicine into a body of a patient to treat infections by the injection.

However, an injection liquid to be injected to the patient is usually processed and stored as a powder for easy storage, and the powder is mixed with a liquid prior to use. In such case, a sealed ampule, in which the powder or the liquid is stored, is opened for use, and when the ampule is opened, since the ampule is made of glass or plastic, fine particles of glass powders (particles) or plastic powders (particles) are generated and contained in the ampule, and the particles are suctioned into the syringe when the liquid medicine is mixed or suctioned. As a result, the particles (contaminants) are injected into the body.

FIG. 7 and FIG. 8 illustrate related art syringe device 1', in which a filter 5 is installed in a syringe needle fixing member 3, and which is equipped with a detachable needle sharp 7 comprising a syringe needle and a syringe needle fixing member and detachably provided at a front end of the syringe, to filter foreign substances such as glass powders (particles) and the like when a mixed or a liquefied medicine is suctioned into a cylinder 8 of a syringe body by using a piston 9. However, the needle sharp 7 used in this case is required to be exchanged before the liquid medicine is injected into the body, to prevent the foreign substance attached to the filter from being injected into a patient when the needle sharp 7 is not exchanged due to carelessness or by mistake.

In addition, when only the needle sharp 7 is exchanged, the syringe may be contaminated by surrounding pathogens (e.g., viruses), and the procedures of use are very cumbersome, and emergency patients may not be quickly treated. In addition, many disposable syringes are used every day, and since a plurality of syringe needles are used for each syringe, medical wastes are exponentially increased, thereby causing adverse effects to the environment. FIGS. 7 and 8 illustrate a safety cover 6 for being placed over the needle sharp 7.

Specifically, medical wastes are separately classified and processed from normal wastes, thereby increasing the processing costs.

In addition, when installing the filter 5, which is installed in the needle sharp 7, because an inner area of the fixing member 3 to which the needle sharp 7 is installed is narrow (as illustrated in FIG. 8), if the filter 5 is installed, the pressure in the needle sharp 7 becomes very high when injecting the liquid medicine due to a bottleneck. Therefore, a large amount of strength is required to press the piston 9 to inject the liquid medicine into the patient, resulting in discomfort to both doctors and patients, and specifically, according to the amount of the liquid medicine to be injected into the infected patient, a lack of proper treatment and side effects to the patients may occur, thereby increasing the risk of safety accidents.

Therefore, to solve these problems, in the present disclosure, a bi-directional filter needle is installed at a fixing member of the syringe needle, wherein the filter needle cannot be used when a different liquid medicine is to be injected to a patient who uses a catheter, during injection, and since the filter needle is installed to the syringe needle, alleviating the pressure problem.

SUMMARY

Therefore, according to various embodiments of the present disclosure, a filter part for filtering foreign substances and the like is installed at a front end of a cylinder of a syringe body such that the filter part can be used in multipurpose applications and the filter part can filter only when the liquid medicine is injected into the body without filtering when the liquid medicine is suctioned.

In addition, the filter part is subject to less pressure when the liquid medicine is injected into the body and the liquid medicine is suctioned without resistance so that convenience of usage is provided to the user.

In addition, when assembling the filter part, the filter can be installed by only inserting the filter into a front end of the syringe body, so an arbitrary detachment of the filter part can be prevented when the liquid medicine is suctioned.

To this end, a filter syringe of the present disclosure includes a protruding part formed at a front end of a cylinder of a syringe body detachably provided thereon with a syringe needle fixing member to which a syringe needle is installed, an inserting part formed at a back end of the protruding part, a rib part protruding from an inner wall of the inserting part at a predetermined length to form a flow path, and a stepping surface formed at an upper end of the rib part.

In addition, a filter part, which is inserted into the inserting part, includes a filter cover and a filter, wherein the filter cover has a predetermined length and includes a body having an inner space, a check wing formed at an end of the body, protruding to an outer circumference of the body, and seated on the step surface of the rib part, and a check valve formed by a step part at a center of an opposite end of the body, and the filter (preferably having a cup shape) is inserted into and fixed to the inner space of the filter part.

Therefore, when liquid medicine is suctioned, only the check wing is opened to open the flow path such that the liquid medicine is suctioned into the cylinder along with the foreign substance (e.g., glass or plastic particles/contaminants existing in an ampule), and when the liquid medicine is injected, the check wing blocks the flow path and the check valve is opened such that the foreign substance is filtered by the filter so that only the liquid medicine is injected.

In addition, the filter is installed in the inner space of the filter cover of the filter part, and due to the thickness of the body of the filter cover, a gap is formed at a side surface of the filter part so that the pressure is dispersed by the gap, thereby allowing ease of injection.

Therefore, according to the various embodiments of the present disclosure, the foreign substance can be filtered when the liquid medicine is suctioned and then discharged by using only the syringe, the filter part is fixed to the syringe by a simple insertion, and the filter part is spaced apart from the inner wall of the inserting part of the syringe to form a gap such that resistance is uniformly applied to an entire part of the filter when the liquid medicine is injected, to disperse pressure so that the syringe can be more easily handled by the medical professionals.

DETAILED DESCRIPTION

According to various embodiments of the present disclosure, a filter syringe includes: a protruding part formed at a front end of a cylinder of a syringe body detachably provided thereon with a syringe needle fixing member to which a syringe needle is installed, an inserting part formed at a back end of the protruding part; a rib part protruding from an inner wall of the inserting part in a predetermined length to form a flow path; a stepping surface formed at an upper end of the rib part; and a filter part, which is inserted into the inserting part, including a filter cover and a filter, wherein the filter cover has a predetermined length and includes a body having an inner space such that the filter cover is closely adhered to the inner wall of the inserting part of the cylinder of the syringe body, a check wing formed at an end of the body, protruding to an outer circumference of the body, and seated on the step surface of the rib part, and a check valve formed by a stepping part at a center of an opposite end of the body, and the filter having a cup shape is inserted into the inner space of the filter cover so that the filter is fixedly coupled to the filter cover while adhering to the filter cover without being arbitrarily detached from the filter cover.

Hereinafter, various embodiments of the present disclosure are described in detail with reference to the accompanying drawings.

Figure 1:
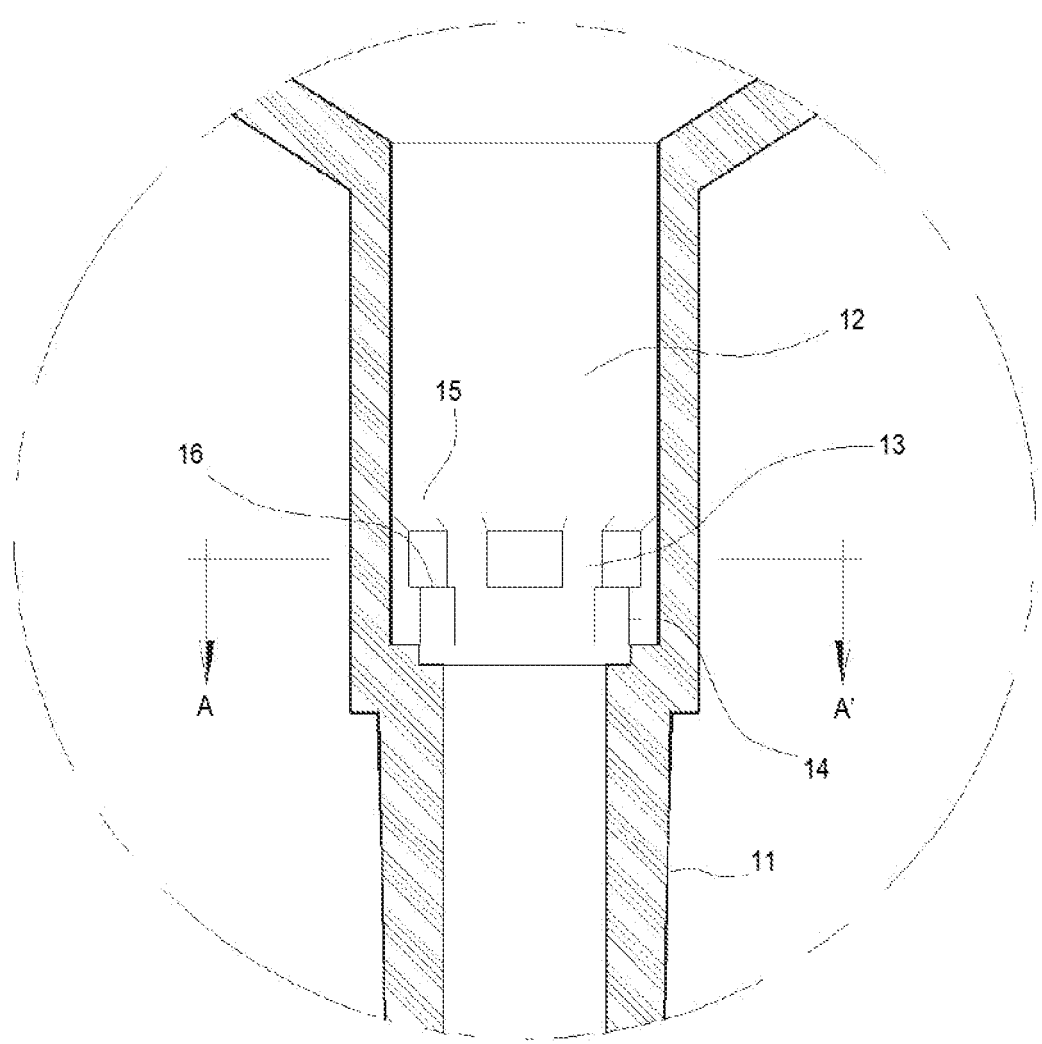
FIG. 1 is a sectional view illustrating a flow path formed by a rib part in an inserting part formed at a cylinder of a syringe of an embodiment of the present disclosure.
Figure 2:
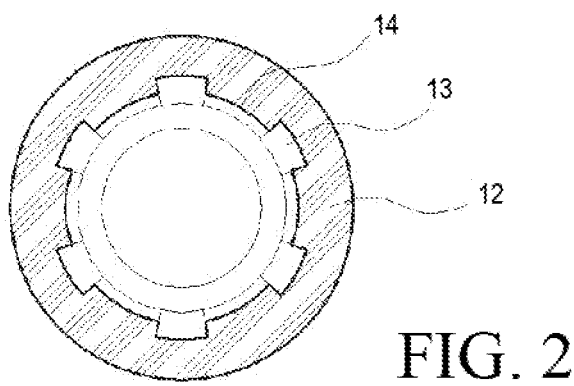
FIG. 2 is a sectional view taken along line A-A' illustrating the flow path formed by the rib part of FIG. 1.
Figure 3:
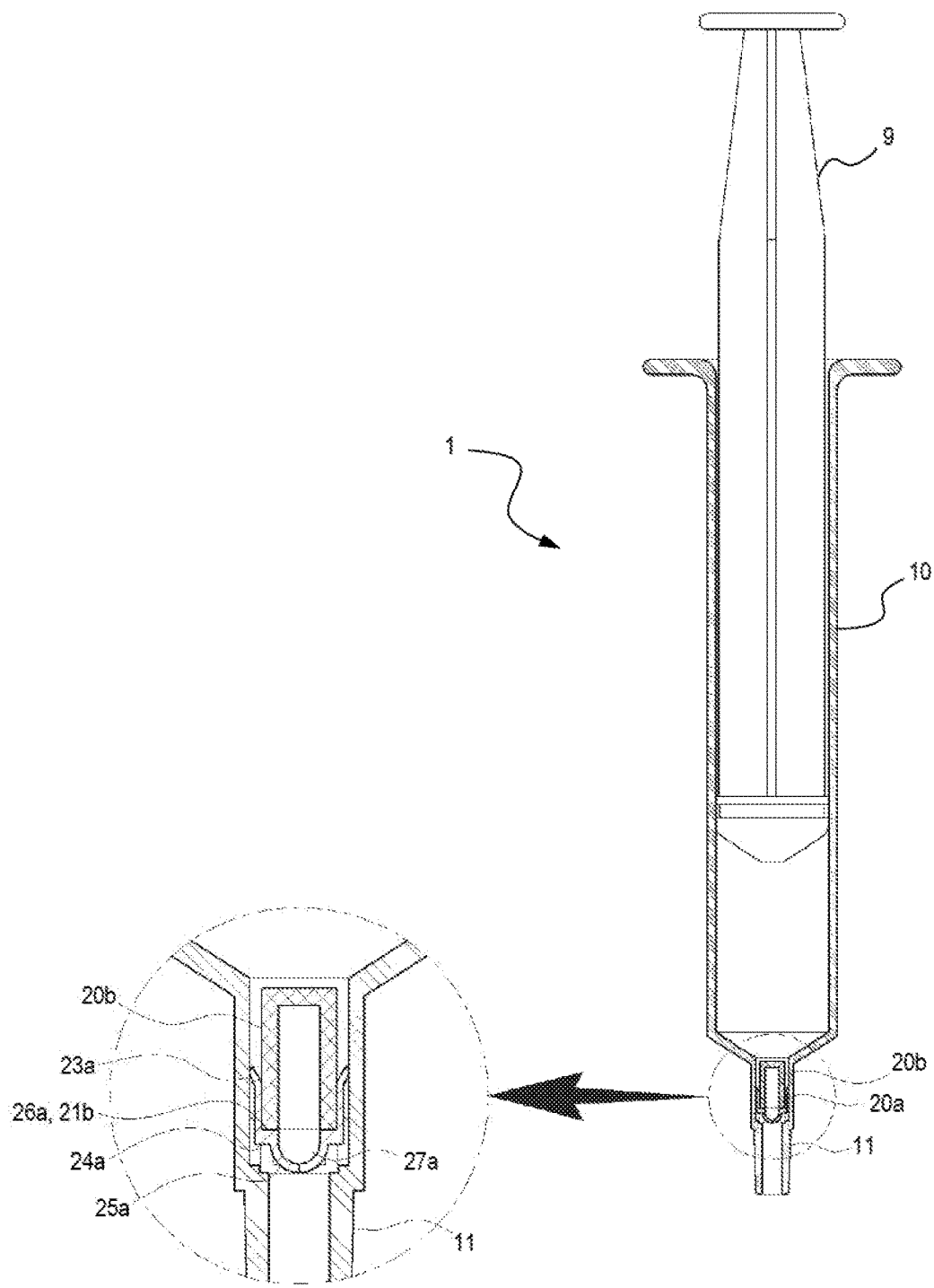
FIG. 3 is a sectional view illustrating a filter part after being inserted into the inserting part of the syringe body of the present disclosure.
Figure 4:
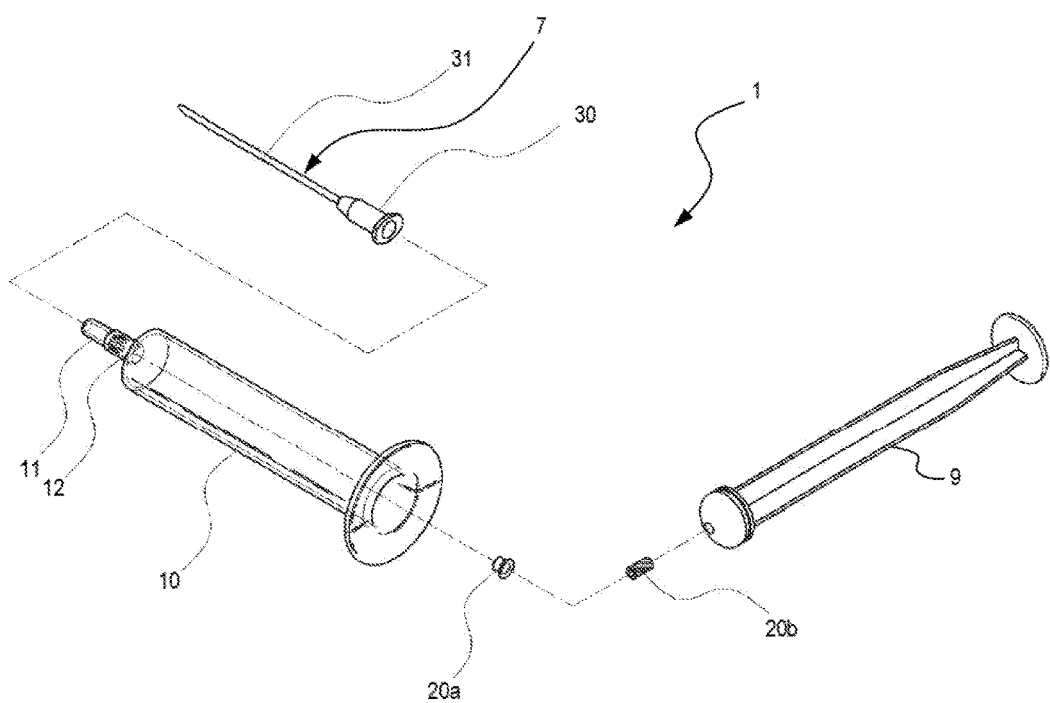
FIG. 4 is an assembled perspective view illustrating a configuration of the syringe of the present disclosure.
Figure 5:
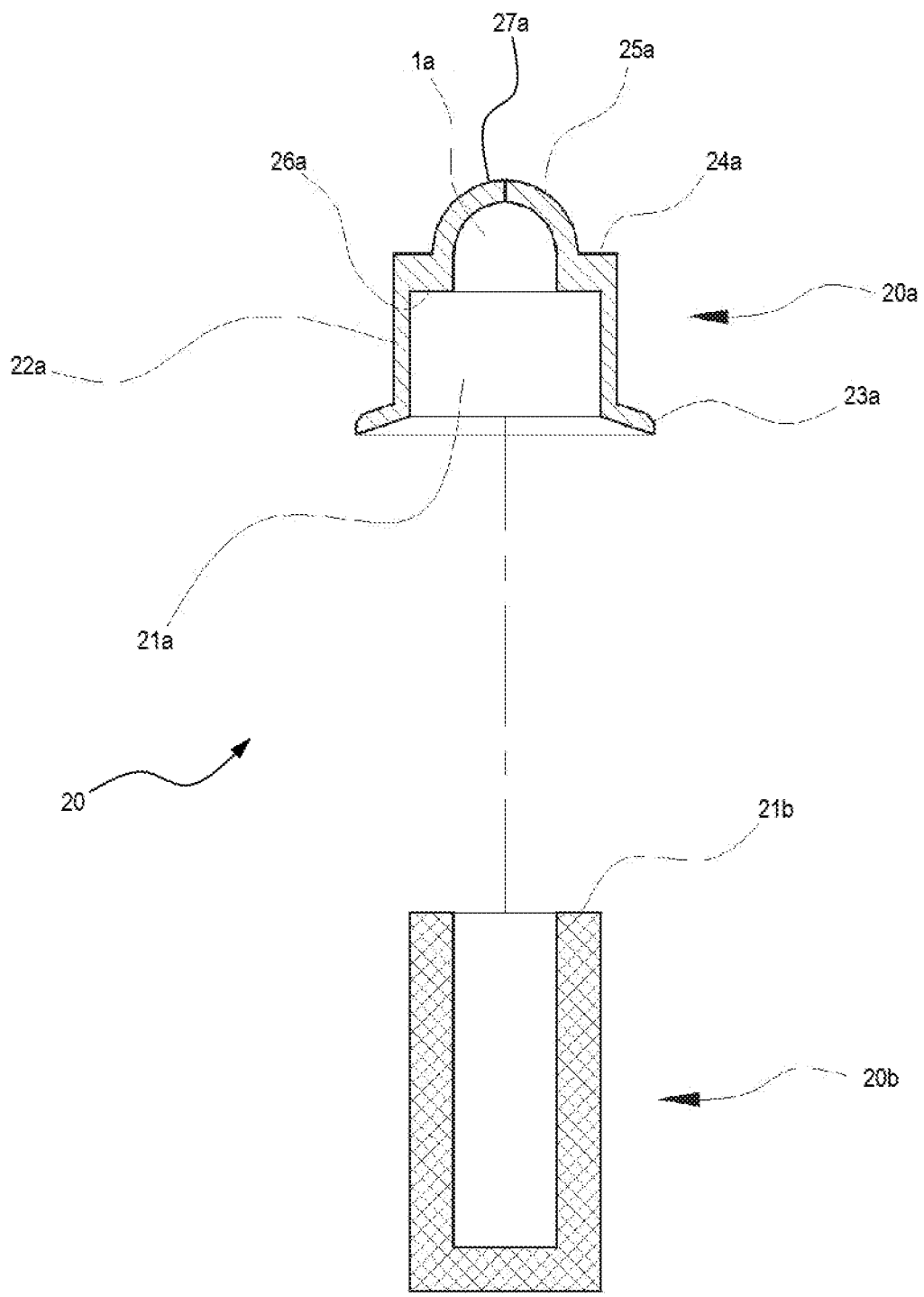
FIG. 5 is an exploded perspective view illustrating a configuration of the filter part of the present disclosure.

The syringe 1, in an embodiment of the present disclosure, as illustrated in FIGS. 1 to 6, generally includes a protruding part 11 formed at a front end of a cylinder 10 of a syringe body detachably provided thereon with a syringe needle fixing member 30 to which a syringe needle 31 is installed, (the syringe needle fixing member 30 and the syringe needle 31 form a detachable needle sharp 7, as illustrated in FIG. 4), and an inserting part 12 (as illustrated in FIGS. 1 and 4) formed at a back end of the protruding part 11, wherein an inner side of the inserting part 12 is formed in a stepwise fashion with the protruding part 11.

In addition, a rib part 14 protrudes from an inner wall of the inserting part 12 in a predetermined length to form a flow path 13, and a stepping surface 15 is slantingly formed toward an inner side in the inner wall at an upper end of the rib part 14, the stepping surface 15 is inclined inwardly and downwardly in such a manner that the syringe 1 is easily opened when liquid medicine is suctioned and the filter 20b is completely attached to the syringe 1 without separation when the liquid medicine is injected, such that the liquid medicine can easily flow when the liquid medicine is injected and no liquid medicine remain in the syringe.

The flow path 13 is radially formed at a constant interval such that pressure is dispersed, and the rib part 14 forming the flow path 13 protrudes in such a manner that the inserting part 12 is stepped from the protruding part 11 coupled to the fixing member 30 of the needle sharp 7.

In this case, a depth of the flow path 13, which is formed by the rib part 14 protruding in a predetermined interval, is formed such that the flow path 13 is completely covered when a filter cover 20a of the filter part 20 (illustrated in FIG. 5) covers the stepping surface 15 formed on an upper part of the rib part 14.

In other words, the depth of the flow path 13 is formed to be smaller than a protruding width of the check wing 23a of the filter part 20 such that the flow path 13 of the check wing 23a may be completely covered.

In addition, the rib part 14 protruding in a predetermined length from the inner wall of the inserting part 12 is defined by multiple steps of the stepping surface 15 formed at the upper end of the inserting part 12 and a seating surface 16 formed at a lower end of the inserting part 12 so that when the filter cover 20a of the filter part 20 is press-fitted into the inserting part 12, the check wing 23a formed on the filter cover 20a is adhered to the stepping surface 15 formed at the upper end of the inserting part 12 while the stepping part 24a, which is distinguished from the check valve 25a of the filter cover 20a, is adhered to the seating surface 16, so that the check valve 25a inserted into the inserting part 12 is exposed without being pressed so that an operation of the check valve 25a is not interrupted.

The check valve 25a has a curved outer surface in such a manner that, when liquid medicine is suctioned, an external force is not transferred to the check valve 25a.

In addition, the flow path 13, which is formed between the rib part 14, is completely covered when the check wing 23a of the filter 20 covers the stepping surface 15 formed on the upper part of the rib part 14.

In addition, the filter part 20, which is inserted into the inserting part 12, having the described configuration includes a filter cover 20a constituted by an elastic material and a filter 20b having a predetermined hardness.

In this case, the filter cover 20a has a predetermined length and includes a body 22a having an inner space 21a such that the filter cover 20a is closely adhered to the inner wall of the inserting part 12 of the cylinder of the syringe body, a check wing 23a formed at an end of the body 22a, protruding to an outer circumference of the body 22a, and seated on the stepping surface 15 of the rib part 14, and a check valve 25a formed by a stepping part 24a at a center of an opposite end of the body 22a, and the filter 20b having a cup shape is inserted into the inner space 21a of the filter cover 20a so that the filter is fixedly coupled to the filter cover while closely adhering to the filter cover without being detached from the filter cover.

In this case, the filter 20b, which is inserted into the inner space 21a of the filter cover, has a cup shape, in which an opened part is directed and inserted into the inner space 21a such that a front end 21b of the filter cover 20a is closely adhered to a supporting surface 26a of the filter cover 20a.

In this case, a width of the supporting surface 26a and a width of the opened front end 21b of the filter 20b are identical so that resistance is not generated when the liquid medicine flows through the filter.

In addition, the filter 20b is press-molded into a cup shape in a predetermined mold after a binder and a bead are make contact by pressure applied to the binder and the bead while a binder is coated on a small bead after the small bead is mixed with the binder so that the liquid medicine is filtered through a gap created between the beads.

Thus, the inner wall of the body 22a of the filter cover 20a is closely adhered to the filter 20b so an arbitrary detachment does not occur.

However, the filter 20b is precisely pressed into a cup shape by a press drawing scheme through using a net having a predetermined supporting strength, and in this case, the filter is not changed even when an interval of a mesh of the net is elongated, so an identical effect may be created even when the filter molded.

In addition, when the filter 20b is inserted into the inner space 21a of the filter cover 20a in the cup shape, due to a thickness of the body 22a of the filter cover 20a and the protrusion of the rib part 14, a gap space 1a, through which the liquid medicine may flow, is formed between the filter cover 20a and the inner wall of the inserting part 12 of the cylinder of the syringe body when the filter 20b is installed so the pressure is dispersed when the liquid medicine is injected, and the filter 20b is long so that the filter 20b protrudes to a backward direction even when the filter (20b) is inserted into and coupled to the inner space (21a) of the filter cover (20a) such that the filter 20b protrudes from the inserting part 12 thus having an excellent dispersion of pressure.

As described above, the filter cover 20a should have excellent elastic force and be hygienic, therefore, according to the present disclosure, silicon is used, however, various materials having identical characteristics with silicon may be used, and this does not limit the object of the present disclosure.

In addition, by the elastic force of the filter cover 20a, when the filter 20b is coupled to the filter cover 20a and the filter cover 20a is inserted into the inserting part 12, the filter 20b and the filter cover 20a are closely fixed.

Figure 6:
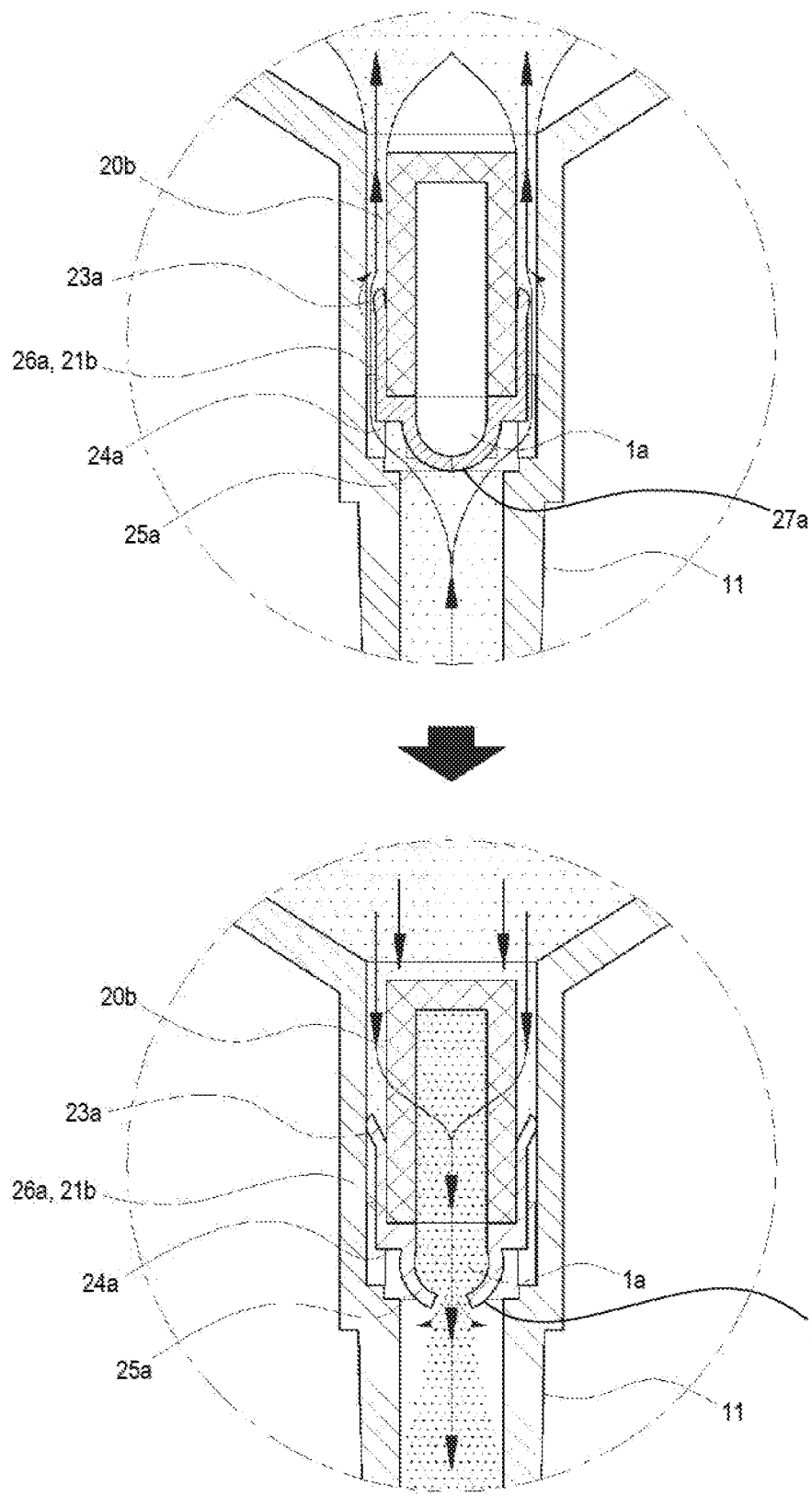
FIG. 6 is a flow chart illustrating a flow of liquid medicine when suctioned and injected according to the present disclosure.
Figure 7:
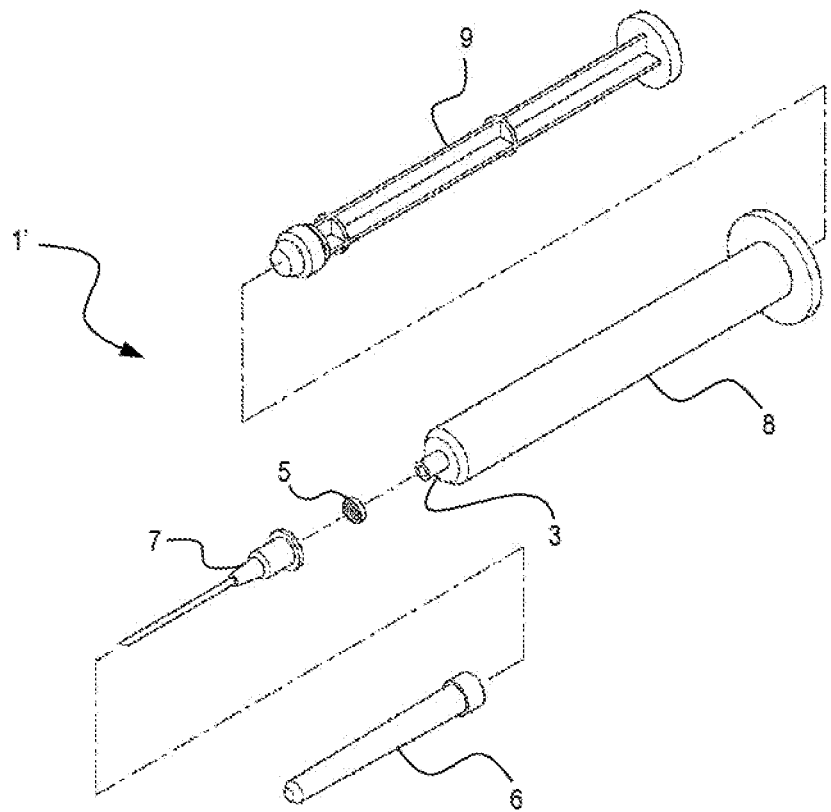
FIGS. 7 and 8 are views illustrating the filter installed to a typical syringe needle, in which the filter is coupled to the syringe body.
Figure 8:
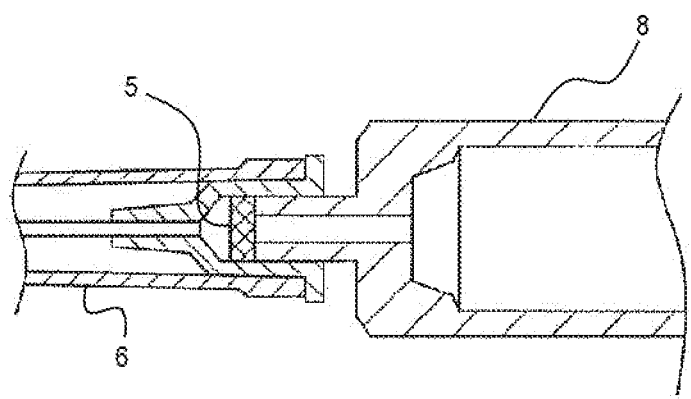

Therefore, when the liquid medicine is suctioned through the syringe needle 31 (i.e., when the piston 9 is pulled or pushed inside the cylinder 10), the pressure is not transferred to the curved check valve 25a when the liquid medicine and the foreign substance is introduced through the protruding part, and when the pressure is generated through the flow path 13, the flow path 13 is opened while the check wing 23a is pushed out so that the liquid medicine is suctioned into the cylinder along with the foreign substance (as illustrated in an upper portion of FIG. 6). In addition, when the liquid medicine is injected, the check wing 23a blocks the flow path 13 by a pressing force, the liquid medicine concentrates (pressurizes) on a curved space or portion 27a formed at a back of the check valve 25a through the filter 20b such that the check valve 25a is opened so that only the foreign substance (e.g., glass and plastic contaminants that may exist in an ampule or the cylinder 10 of the syringe 1) is filtered by the filter 20b and only the liquid medicine is injected through the check valve 25a after being filtered by the filter 20b (as illustrated in a lower portion of FIG. 6).

In this case, the liquid medicine is dispersed by the gap space 1a (illustrated in FIGS. 5 and 6), by which the protrusion of the filter 20b and the protruded filter 20b are spaced apart from the inner wall of the inserting part 12, so the syringe 1 may inject the liquid medicine without counter pressure.

In addition, the required liquid medicine, filtered in the manner above, may be delivered into the human body via a catheter, a syringe needle, or a combination thereof.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A filter syringe comprising:
a syringe body comprising a cylinder;
an inserting part formed at an end of the cylinder;
a protruding part formed an end of the inserting part, such that the inserting part is positioned between the protruding part and the cylinder;
a needle sharp comprising a syringe needle attached to a syringe needle fixing member, the syringe needle fixing member configured to be detachably installed on the inserting part;
a rib part protruding from an inner wall of the inserting part in a predetermined length to form a flow path;
a stepping surface formed at an end of the rib part; and
a filter part configured to be inserted into the inserting part, the filter part comprising a filter cover and a filter,
wherein the filter cover comprises a predetermined length and a filter body having an inner space, such that when the filter part is inserted into the inserting part, the filter cover is closely attached to the inner wall of the inserting part,
wherein the filter cover comprises:
a check wing formed at an end of the filter body, the check wing protruding from an outer circumference of the filter body, and the check wing is configured to be seated on the stepping surface of the rib part, and
a check valve formed at a stepping part of the filter body,
wherein the filter having a cup shape is insertable into the inner space of the filter body so that the filter is fixedly coupled to the filter cover while closely being adhered to the filter cover without being arbitrarily detached from the filter cover, wherein, when liquid is suctioned into the syringe body, the check wing is configured to flex in a first direction of liquid flow, to create a flow passage in the protruding part, and wherein, when the liquid is injected from the filter syringe, the check wing is further configured to resist flexing in the first direction of liquid flow, such that the liquid is forced to flow in a second direction, through the filter and out of the check valve.

2. The filter syringe of claim 1, wherein the stepping surface is inclined inwardly and downwardly so that the syringe is easily opened when liquid medicine is suctioned, and wherein the filter is completely adhered to the syringe without separation therefrom when the liquid medicine is injected, so that the liquid medicine flows with reduced restriction when the liquid medicine is injected and no liquid medicine remains in the syringe.

3. The filter syringe of claim 1, wherein the flow path is radially formed at a constant interval such that suction pressure is dispersed, and wherein the rib part forming the flow path protrudes so that the inserting part is stepped from the protruding part coupled to the fixing member of the syringe needle.

4. The filter syringe of claim 1, wherein the rib part protruding from the inner wall of the inserting part is defined by the stepping surface formed at the upper end of the inserting part and a seating surface formed at a lower end of the inserting part such that, when the filter cover of the filter part is press-fitted onto the inserting part, the check wing formed on the filter cover is adhered to the stepping surface formed at the upper end of the inserting part while the stepping part of the filter cover is adhered to the seating surface, such that the check valve inserted onto the inserting part is exposed without being pressed such that an operation of the check valve is not interrupted.

5. The filter syringe of claim 4, wherein the check valve has a curved outer surface and an inner surface forming a curved space so that, an external force is not transferred to the check valve when liquid medicine is suctioned and the fluid path of the syringe is facilitated when the liquid medicine is injected from the syringe.

6. The filter syringe of claim 4, wherein the filter comprises an opened part that is configured to be directed and inserted into the inner space of the filter body, such that a front end of the filter cover is closely adhered to a supporting surface.

7. The filter syringe of claim 1, wherein the filter is press-molded into the cup shape while a binder is coated on a small bead after the small bead is mixed with the binder to filter liquid medicine through a gap created between the beads.

8. The filter syringe of claim 6, further comprising:

a gap space formed between the filter cover and the inner wall of the inserting part of the cylinder of the syringe body when the filter is inserted into the inner space of the filter cover, due to a thickness of the body cover of the filter cover and a protrusion of the rib part, such that the filter protrudes to a backward direction even when the filter is inserted into and coupled to the inner space of the filter cover to facilitate dispersion of pressure.

* * * * *